US 8,617,802 B2

(12) United States Patent
Köhl et al.

(10) Patent No.: US 8,617,802 B2
(45) Date of Patent: Dec. 31, 2013

(54) ORGAN TRANSPLANT SOLUTIONS AND METHOD FOR TRANSPLANTING ORGANS

(75) Inventors: Jörg Köhl, Cincinnati, OH (US); Prasad Devarajan, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 1227 days.

(21) Appl. No.: 12/239,158

(22) Filed: Sep. 26, 2008

(65) Prior Publication Data

US 2009/0311663 A1    Dec. 17, 2009

Related U.S. Application Data

(63) Continuation of application No. 11/368,935, filed on Mar. 6, 2006, now abandoned.

(60) Provisional application No. 60/660,571, filed on Mar. 11, 2005.

(51) Int. Cl.
*A01N 1/02*      (2006.01)
*A61K 38/16*     (2006.01)
*A61K 38/00*     (2006.01)
*C12M 1/00*      (2006.01)

(52) U.S. Cl.
USPC ....... 435/1.2; 435/1.1; 435/283.1; 435/284.1; 514/1.1; 514/21.3

(58) Field of Classification Search
None
See application file for complete search history.

(56) References Cited

U.S. PATENT DOCUMENTS

| | | |
|---|---|---|
| 4,798,824 A | 1/1989 | Belzer et al. |
| 4,879,283 A | 11/1989 | Belzer et al. |
| 5,145,771 A | 9/1992 | Lemasters et al. |
| 5,506,121 A | 4/1996 | Skerra et al. |
| 5,693,462 A | 12/1997 | Raymond |
| 5,912,019 A | 6/1999 | Singh |
| 6,022,951 A | 2/2000 | Sano et al. |

FOREIGN PATENT DOCUMENTS

| | | |
|---|---|---|
| WO | WO 88/05044 | 7/1988 |
| WO | WO 03/078457 | 9/2003 |

OTHER PUBLICATIONS

Lewis,AG; Kohl,G; Mab,Q; Devarajan,P; Kohl,J "C5a receptor blockade as a new therapeutic concept in kidney transplantation" Molecular Immunology (XIth European meeting on Complement in Human Disease, Abstract O13), Sep. 2007, 44 (16),pp. 3914-3915.*
Otto,M; Hawlisch,H;Monk,PN;Muller,M;Klos,A;Karp,CL;Kohl,J "C5a Mutants are Potent Antagonists of the C5a Receptor (CD88) and of C5L2: Position 69 Is the Locus That Determines Agonism or Antagonism" JBC, Jan. 2, 2004 (published Oct. 21, 2003), 279(1), pp. 142-151.*
Haugland, R., Handbook of Flourescent Probes and Research Chemicals, 6$^{th}$ Ed. (1996) Molecular Probes, Eugen, OR, p. 96.
Heller, T. et al., "Selection of a C5a Receptor Antagonist from Phage Libraries Attentuating the Inflammatory Response in Immune Comples Disease and Ischemia/Reperfusion Injury," J. of Immunology, vol. 163(2) (Jul. 15, 1999) pp. 985-994.
Hennecke, M. et al., "A Selection System to Study C5aC5a-Receptor Interactions; Phage-Display of a Novel C5a Anaphylatoxin, Fos-C5a$^{Ala27}$", Gene vol. 184(2) (1997) pp. 263-272.
Pellas et al., "Novel C5a receptor antagonists regulate neutrophil functions in vitro and in vivo," J. of Immunology, vol. 160(11) (Jun. 1, 1998) pp. 5616-5621.
Devries, et al., Complement Factor C5a Mediates Renal Ischemia-Reperfusion Injury Independent from Neutrophils, The Journal of Immunology, 2003, pp. 3883-3889, vol. 179, No. 7, The American Association of Immunologists, Inc.
Gueler, et al., Complement 5a Receptor Inhibition Improves Renal Allograft Survival, Journal of the American Society of Nephrology, 2008, pp. 2302-2312, vol. 19, No. 12.
Lewis, et al., Pharmacological targeting of C5a receptors during organ preservation improves kidney graft survival, Clinical & Experimental Immunology, The Journal of Translational Immunology, 2008, pp. 117-126, vol. 153, Issue 1, British Society for Immunology.

* cited by examiner

*Primary Examiner* — Chris R Tate
*Assistant Examiner* — Aaron J Kosar
(74) *Attorney, Agent, or Firm* — Frost Brown Todd LLC

(57) ABSTRACT

A preservation solution for organs waiting to be transplanted is disclosed; the method of using the solution in a transplantation procedure is also disclosed. The preservation solutions comprise a balanced isotonic aqueous solution comprising sodium, potassium, calcium, magnesium and bicarbonate ions in a physiologically acceptable amount, together with an effective amount of a mutein of the C5*a* anaphylatoxin which is a C5*a* receptor antagonist wherein the amino acid residue naturally occurring at sequence position 69 is mutated.

19 Claims, No Drawings

SEQUENCE LISTING

```
<160> NUMBER OF SEQ ID NOS: 19

<210> SEQ ID NO 1
<211> LENGTH: 7
<212> TYPE: PRT
<213> ORGANISM: Artificial Sequence
<220> FEATURE:
<223> OTHER INFORMATION: C5aR

<400> SEQUENCE: 1

Phe Lys Arg Ser Leu Leu Arg
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: C5aR

<400> SEQUENCE: 2

Phe Lys Arg Leu Leu Leu Arg
1               5

<210> SEQ ID NO 3
<211> LENGTH: 5
<212> TYPE: PRT
<213> ORGANISM: Artificial Sequence
<220> FEATURE:
<223> OTHER INFORMATION: C5aR

<400> SEQUENCE: 3

Phe Lys Arg Ser Cys
1               5

<210> SEQ ID NO 4
<211> LENGTH: 7
<212> TYPE: PRT
<213> ORGANISM: Artificial Sequence
<220> FEATURE:
<223> OTHER INFORMATION: C5aR

<400> SEQUENCE: 4

Phe Lys Arg Ser Leu Leu Cys
1               5

<210> SEQ ID NO 5
<211> LENGTH: 7
<212> TYPE: PRT
<213> ORGANISM: Artificial Sequence
<220> FEATURE:
<223> OTHER INFORMATION: C5aR

<400> SEQUENCE: 5

Phe Lys Arg Leu Leu Leu Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: C5aR

<400> SEQUENCE: 6

Phe Lys Lys Ala Leu Leu Arg
1               5

<210> SEQ ID NO 7
<211> LENGTH: 4
<212> TYPE: PRT
<213> ORGANISM: Artificial Sequence
<220> FEATURE:
<223> OTHER INFORMATION: C5aR

<400> SEQUENCE: 7

Phe Lys Arg Ser
1
```

```
<210> SEQ ID NO 8
<211> LENGTH: 7
<212> TYPE: PRT
<213> ORGANISM: Artificial Sequence
<220> FEATURE:
<223> OTHER INFORMATION: C5aR

<400> SEQUENCE: 8

Phe Lys Leu Leu Leu Leu Arg
 1               5

<210> SEQ ID NO 9
<211> LENGTH: 73
<212> TYPE: PRT
<213> ORGANISM: Homo Sapiens
<220> FEATURE:
<223> OTHER INFORMATION: (C5a-(1-66,Cys27Ala)-A8B

<400> SEQUENCE: 9

Thr Leu Gln Lys Lys Ile Glu Glu Ile Ala Ala Lys Tyr Lys His Ser
 1               5                  10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser Phe Lys Arg Ser Leu Leu Arg
65                  70

<210> SEQ ID NO 10
<211> LENGTH: 73
<212> TYPE: PRT
<213> ORGANISM: Homo Sapiens
<220> FEATURE:
<223> OTHER INFORMATION: (C5A-(1-66,Cys27Ala)-A8B-Leu70

<400> SEQUENCE: 10

Thr Leu Gln Lys Lys Ile Glu Glu Ile Ala Ala Lys Tyr Lys His Ser
 1               5                  10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser Phe Lys Arg Leu Leu Leu Arg
65                  70

<210> SEQ ID NO 11
<211> LENGTH: 71
<212> TYPE: PRT
<213> ORGANISM: Homo Sapiens
<220> FEATURE:
<223> OTHER INFORMATION: (C5a(1-66,Cys27Ala)-A8B-Cys71)

<400> SEQUENCE: 11

Thr Leu Gln Lys Lys Ile Glu Glu Ile Ala Ala Lys Tyr Lys His Ser
 1               5                  10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45
```

```
Lys Ala Phe Thr Glu Cys Cys Val Val Ala Ser Gln Leu Arg Ala Asn
    50                  55                  60

Ile Ser Phe Lys Arg Ser Cys
65                  70

<210> SEQ ID NO 12
<211> LENGTH: 73
<212> TYPE: PRT
<213> ORGANISM: Homo Sapiens
<220> FEATURE:
<223> OTHER INFORMATION: (C5a-(1-66,Cys27Ala)-A8B-Cys73)

<400> SEQUENCE: 12

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
    50                  55                  60

Ile Ser Phe Lys Arg Ser Leu Leu Cys
65                  70

<210> SEQ ID NO 13
<211> LENGTH: 73
<212> TYPE: PRT
<213> ORGANISM: Homo Sapiens
<220> FEATURE:
<223> OTHER INFORMATION: (C5a(1-66, Cys27Ala)-A8B-Leu70-Tyr73)

<400> SEQUENCE: 13

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
    50                  55                  60

Ile Ser Phe Lys Arg Leu Leu Leu Tyr
65                  70

<210> SEQ ID NO 14
<211> LENGTH: 73
<212> TYPE: PRT
<213> ORGANISM: Homo Sapiens
<220> FEATURE:
<223> OTHER INFORMATION: (C5a-(1-66, Cys27Ala)-A8B-Lys69-Ala70)

<400> SEQUENCE: 14

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
    50                  55                  60

Ile Ser Phe Lys Lys Ala Leu Leu Arg
```

<210> SEQ ID NO 15
<211> LENGTH: 73
<212> TYPE: PRT
<213> ORGANISM: Homo Sapiens
<220> FEATURE:
<223> OTHER INFORMATION: (C5a(1-66,Cys27Arg)-A8b)

<400> SEQUENCE: 15

Thr Leu Gln Lys Lys Ile Glu Glu Ile Ala Ala Lys Tyr Lys His Ser
1               5                   10                  15

Val Val Lys Lys Cys Cys Tyr Asp Gly Ala Arg Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser Leu Leu Arg
65                  70

<210> SEQ ID NO 16
<211> LENGTH: 70
<212> TYPE: PRT
<213> ORGANISM: Homo Sapiens
<220> FEATURE:
<223> OTHER INFORMATION: (C5a-(1-66,Cys27Ala)-A8B-Del 71-73)

<400> SEQUENCE: 16

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser
65                  70

<210> SEQ ID NO 17
<211> LENGTH: 76
<212> TYPE: PRT
<213> ORGANISM: Homo Sapiens
<220> FEATURE:
<223> OTHER INFORMATION: (C5a-(1-66,Cys-3,Gly-2,-1,Cys27Ala)-A8B)

<400> SEQUENCE: 17

Cys Gly Gly Thr Leu Gln Lys Lys Ile Glu Glu Ile Ala Ala Lys Tyr
1               5                   10                  15

Lys His Ser Val Val Lys Lys Cys Cys Tyr Asp Gly Ala Arg Val Asn
            20                  25                  30

Asn Asp Glu Thr Cys Glu Gln Arg Ala Ala Arg Ile Ser Leu Gly Pro
        35                  40                  45

Arg Cys Ile Lys Ala Phe Thr Glu Cys Cys Val Val Ala Ser Gln Leu
    50                  55                  60

Arg Ala Asn Ile Ser Phe Lys Arg Ser Leu Leu Arg
65                  70                  75

<210> SEQ ID NO 18
<211> LENGTH: 73

```
<212> TYPE: PRT
<213> ORGANISM: Homo Sapiens
<220> FEATURE:
<223> OTHER INFORMATION: (C5a-(1-66,Cys27Ala)A5a)

<400> SEQUENCE: 18

Thr Leu Gln Lys Lys Ile Glu Glu Ile Ala Ala Lys Tyr Lys His Ser
 1               5                  10                  15

Val Val Lys Lys Cys Cys Tyr Asp Gly Ala Arg Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Leu Leu Leu Arg
65                  70

<210> SEQ ID NO 19
<211> LENGTH: 11
<212> TYPE: PRT
<213> ORGANISM: Artificial Sequence
<220> FEATURE:
<223> OTHER INFORMATION: Linker

<400> SEQUENCE: 19

Cys Gly Gly Gly Gly Ser Gly Gly Gly Gly Ser
 1               5                  10
```

ORGAN TRANSPLANT SOLUTIONS AND METHOD FOR TRANSPLANTING ORGANS

CROSS-REFERENCE TO RELATED APPLICATIONS

This application claims the benefit of U.S. Provisional Application 60/660,571, Kohl et al., filed Mar. 11, 2005, incorporated herein by reference in its entirety. This application is a continuation of U.S. non-provisional application Ser. No. 11/368,935, filed Mar. 6, 2006 now abandoned.

TECHNICAL FIELD

The present invention relates to organ preservation solutions and to methods for transplanting organs. More particularly, this invention relates to preservation solutions for perfusing and storing an organ while awaiting implantation and to methods of using the preservation solution during transplantation of the organ.

BACKGROUND OF THE INVENTION

A great deal of research progress has been made over the years in understanding cellular mechanisms, as well as developing new transplantation techniques, for keeping organs viable not only during storage but also after reperfusion of these organs (e.g., minimization of ischemia/reperfusion injury). As a result, organ transplantation has become an established and effective technique. A significant factor limiting clinical application of organ transplantation is decrease in viability of the organ after removal from the donor.

Generally, the two most frequently used methods for preserving organs after removal from the donor are simple hypothermic storage and continuous pulsatile perfusion. With simple hypothermic storage, the organ is removed from the donor and cooled rapidly. This is usually achieved by a combination of cooling and short periods of perfusion to drop the organ temperature as quickly as possible to a temperature between 0° C. and 4° C., where it may be held for up to about six hours. While cold storage enables organs to be transplanted, the time during which the organ is viable is short. Cold storage decreases the rate at which intracellular enzymes, essential cellular components necessary for organ viability, degrade but does not stop metabolism entirely.

The second method of organ preservation which has undergone extensive investigation, continuous pulsatile perfusion, utilizes the following elements: (1) pulsatile flow, (2) hypothermia, (3) membrane oxygenation, and (4) a perfusate containing both albumin and lipids. Although being more technically complex and costly, continuous pulsatile perfusion provides significantly longer viability of the organ when compared to simple hypothermia.

Preserving organs at between 0° C. and 4° C. can result in damage to the organ during storage and upon reperfusion with a warm reperfusion solution. Injury to the organ occurs through damage to epithelial and endothelial cells. Although some of the solutions of the prior art have been useful to extend the storage time of donor organs and lessen injury to the organ upon reperfusion, cell injury still does occur frequently. It is desirable to extend the viable organ life and improve the quality of the transplanted organ. For example, using preservation solutions of the prior art, kidneys that have been in cold storage beyond 48 hours frequently cannot be used and must be discarded. Extending organ viability allows sufficient time for compatibility testing of the donor and recipient, and increased organ availability. It is also desirable to minimize damage to the organ upon reperfusion. Ischemia-reperfusion injury to transplanted organs preserved in solutions of the prior art commonly results in delayed graft function, and predisposes the graft to acute and chronic rejection.

A storage solution for preserving organs which can be used at temperatures from 0° C. to 37° C. is disclosed in U.S. Pat. No. 5,145,771, Lemasters et al., issued Sep. 8, 1992. The solution requires the use of a colloid, hydroxyethyl starch for osmotic support against interstitial edema.

U.S. Pat. Nos. 4,879,283 and 4,798,824, Belzer et al., issued Nov. 7, 1989 and Jan. 17, 1989, respectively, relate to organ preservation/storage solutions containing a specifically defined synthetic hydroxyethyl starch in place of human serum albumin. These patents cover the widely used organ preservation solution commercially available under the trade name VIASPAN™, marketed by Barr Laboratories.

International Published Patent Application WO 03/078457, published Sep. 25, 2003, describes muteins of the C5a anaphylatoxin, which are taught to be C5a receptor antagonists. The materials are taught to be useful for the treatment of C5a-mediated disease or inflammatory conditions, such as asthma, adult respiratory distress syndrome, ischemia/reperfusion injury, chronic progressive pulmonary cystic fibrosis, and rheumatoid arthritis. It is also taught that the C5a muteins can be used to treat patients suffering from organ transplant rejection.

The present invention provides preservation solutions useful for storing organs while awaiting implantation which extend the vitality of the organ and reduce damage to organ cells. The present invention also provides method for preserving organs which extend the maximum life of the organ during transplantation.

SUMMARY OF THE INVENTION

In accordance with these objectives, there are disclosed preservation solutions for use in the transplantation of organs, and to methods for transplanting organs using those solutions, which methods increase storage times and lessen injury to the organs. The preservation solutions of the present invention comprise:
  (a) a balanced isotonic solution comprising sodium, potassium, calcium, magnesium and bicarbonate ions in a physiologically acceptable amount;
  (b) a safe and effective amount of a mutein of the C5a anaphylatoxin which is a C5a receptor antagonist, wherein the amino acid residue naturally occurring at sequence position 69 is mutated; and
  (c) water.

The present invention also relates to a method for preservation, storage and reperfusion of organs intended for implantation, said method comprising:
  preserving or perfusing said organ with a solution comprising:
  (a) a balanced isotonic solution comprising sodium, potassium, calcium, magnesium and bicarbonate ions in a physiologically acceptable amount;
  (b) a safe and effective amount of a mutein of the C5a anaphylatoxin which is a C5a receptor antagonist, wherein the amino acid residue naturally occurring at sequence position 69 is mutated; and
  (c) water.

Finally, the present invention relates to a method of preserving organs intended for implantation, said method comprising perfusing the body of the dead organ donor, prior to removal of the organs, with the preservation solution defined above.

The preservation solution in one embodiment includes at least one antioxidant, such as dimethyl thiourea (DMTU), catalase as a hydrogen peroxide scavenger, and apoferritin to decrease iron content within the preservation solution. In addition, the preservation solutions optionally may include hormones, such as insulin and protaglandin, and antibiotics.

All patents and publications cited in this patent are fully incorporated by reference herein.

DETAILED DESCRIPTION OF THE INVENTION

The present invention is directed to new preservation solutions for storing and perfusing organs intended for implantation in a patient requiring such implant. Suitable organs on which the solutions of this invention may be used include, for example, heart, liver, kidney, lungs, intestines, and pancreas.

The individual components of the present invention are all nontoxic and have been found to be stable during storage.

The preservation solutions of the present invention are based on a balanced isotonic solution including sodium, potassium, calcium and magnesium ions, as well as glucose and sodium bicarbonate, in a physiologically acceptable amount. Certain of these types of solutions are well known, such as the one described below, known as Krebs-Henseleit-bicarbonate solution, which has the following composition:

TABLE 1

| Concentration ranges in 1 Liter | |
|---|---|
| NaCl | 85.0 mM to 145 mM |
| KCl | 3.0 mM to 30 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15.0 mM to 35 mM |
| Glucose | 1.0 mM to 50 mM |

Isotonic preservation solutions are also described in U.S. Pat. No. 5,693,462, Raymond, issued Dec. 2, 1997, incorporated herein by reference.

The preservation solutions are designed to prevent or inhibit various mechanisms which cause injury to the organ, and thus should be a composition that performs one or more (and preferably all) of the following functions: (1) prevents or restricts intracellular acidosis, (2) prevents the expansion of intracellular space, (3) prevents injury from oxygen-derived free radicals, especially during reperfusion, (4) enables the regeneration of high-energy phosphate compounds during reperfusion, (5) sustains appropriate metabolic requirements and prevents the rapid changes in intracellular $Na^+$—$H^+$—$Ca^{++}$ following reperfusion.

While the preservation solution begins with the balanced isotonic solution described above, there may be significant differences in the final compositions. For example, the preservation solution begins with the isotonic solution, wherein the potassium concentration is maintained at preferably from about 3.0 mM to about 8.0 mM. Magnesium chloride may be used in place of potassium chloride.

To the balanced isotonic solution is added a safe and effective amount of the C5a mutein which is described in International Published Patent Application WO 03/078457, published Sep. 25, 2003, incorporated herein by reference. By "safe and effective amount" is meant that amount of C5a mutein which provides the beneficial preservation effect and minimization of ischemic perfusion injury, but not so much as to cause damage to the organ or desired side effects to the organ recipient. The C5a mutein is preferably incorporated in the composition at a concentration of from about 0.1 µM to about 10 µM. While not intending to be bound by theory, it is believed that the C5a mutein binds to the C5a receptor sites on the organ thereby reducing ischemic perfusion injury and, as a result, reducing the potential for rejection of the organ upon transplantation.

The mutein used in the present invention can be derived from the natural C5a sequence of mammal and non-mammal species. It can, for instance be of human, porcine, murine, bovine or rat origin. In one embodiment, the mutein is a mutant protein of the human C5a protein.

In one embodiment, the positively charged amino acid residue at sequence position 69 of the C5a mutein is Arg or Lys.

In a further embodiment used in the invention, the mutein comprises a hydrophobic amino acid residue at sequence position 67. The aromatic hydrophobic amino acids Trp, Phe and Tyr are particularly preferred as residues at sequence position 67.

Also preferred antagonists are muteins which comprise a hydrophobic amino acid residue at one or more of the sequence positions 70, 71 or 72. Such hydrophobic amino acid residues can be selected independently from each other, they can be identical or different. Preferred hydrophobic residues are Leu, Ile and Ala.

Such muteins preferably comprise, at sequence position 70. an amino acid residue which is selected from Ala or Leu. Other preferred muteins comprise Ser at sequence position 70.

A preferred amino acid at sequence position 71 is Leu. The antagonistic mutein disclosed can also preferably comprise a Leu residue at sequence position 72.

In a particularly preferred embodiment, the mutein comprises Leu at all of the sequence positions 70, 71, and 72.

If present, i.e., not deleted, in the C5a mutant, the sequence position 73 is preferably occupied by a Cys, Tyr, Arg or Ser residue. In preferred embodiments the mutein has a length of 70, 71, 72 or 73 amino acid residues. In general, Arg, Cys, Tyr or Ser are also preferred as C-terminal amino acid residues of a truncated mutein, i.e., a mutein having 70, 71, 72, or 73 amino acid residues. An example of a mutein having a length of 70 amino acids is the mutein C5a-(1-66, Cys27Ala)-FKRS-70 (cf. Table 1, SEQ ID NO: 16).

Further, muteins are also within the scope of the invention in which the positively charged amino acid at position 69 is the C-terminal (last) residue. Accordingly, such muteins can have a length of 69 amino acids. However, it is also possible to introduce deletions, for example, into the N-terminal region of the protein so that an antagonistic protein used herein can comprise fewer than 69 amino acid residues. For clarity reasons it is noted once again that such deletions can, of course, also be present in muteins of the invention in which residues at sequence positions 70 to 74 are not or only partly deleted.

The mutein used in the present invention preferably comprises or has as C-terminal sequence a sequence selected from the group consisting of 67-FKRSLLR-73 (cf. mutein ABB; SEQ ID NO: 14), 67-FKRLLLR-73 (cf. mutein A8B-Leu-70; SEQ ID NO: 15), 67-FKRSC-71 (cf. mutein Ab8-Cys71, SEQ ID NO: 16), 67-FKRSLLC-73 (cf. mutein Ab8-Cys73, SEQ ID NO: 17), 67-FKRLLLY-73 (cf. mutein A8B-Leu70-Tyr73, SEQ ID NO: 18), 67-FKKALLR-73 (cf. mutein A8B-Lys69Ala70; SEQ ID NO: 19), 67-FKRS-70 (cf. A8B-Del.71-73, SEQ ID NO: 21) and 67-FKLLLLY-73 (cf. A5a, SEQ ID NO: 39). For the sake of clarity, the numbering refers to the amino acid position of C5a, i.e., 67-F means that phenylalanine is present as amino acid at sequence position 67.

The mutein can further comprise an Arg residue at sequence position 27, see, for example, mutein C5a-(1-66, Cys27Arg)-FKRSLLR (A8B-Arg27, SEQ ID NO: 15). In fact, Arg at position 27 is found in porcine and bovine C5a. In addition, muteins of human C5a with a Cys27Arg replacement were selected from C5a mutant phage library (Cain, S., et al. "Analysis of receptor/ligand interactions using whole-molecule randomly-mutated ligand libraries," J. Immunol. Methods. 2000. pp 139-145, 245), incorporated herein by reference. Muteins of C5a with only a Cys27Arg replacement are agonists of the C5a receptor (Ibid.).

Particularly preferred is a mutein of the human C5a anaphylatoxin having or comprising the amino acid sequence of SEQ ID NO: 9, i.e., C5a-(1-66, Cys27Ala-)A8B; SEQ ID NO: 10, i.e., C5a-(1-66, Cys27Ala)-A8B-Leu 70; SEQ ID NO: 11, i.e., C5a-(1-66, Cys27Ala)-A8B-Cys71; SEQ ID NO: 12, i.e., C5a-(1-66, Cys27Ala)-A8B-Cys73; SEQ ID NO: 13; i.e., C5a-(1-66, Cys27Ala)-A8B-Leu70-Tyr73); SEQ ID NO: 14, i.e., C5a-(1-66, Cys27Ala)-A8B-Lys69-Ala70); SEQ ID NO: 15; i.e., C5a-(1-66, Cys27Arg)-A8B; SEQ ID NO: 16, i.e., C5a-(1-66, Cys27Ala)-A8B-Del.71-73); SEQ ID NO: 17, i.e., C5a-(1-66, Cys-3, Gly-2,-1, Cys27Ala)-A8B; and SEQ ID NO: 18, i.e., C5a-(1-66, Cys27Ala)A5a.

A mutant C5a antagonist of the present invention cannot only be present as the isolated (recombinant) protein but it can also be modified. In one embodiment, a mutein of the invention can be dimerized either with the same or a different mutein to form a homo- or heterodimer. For this purpose the mutein can comprise an N-terminal linker sequence which is capable of dimerizing the C5a mutein. One example of a preferred linker sequence linked to the N-terminus comprises the sequence Cys-Gly-Gly which can be used for spontaneous dimerization of the C5a mutein A8B in the course of the recombinant production of the mutant protein (cf. the mutein C5a-(1-66; Cys-3, Gly-2,-1; Cys27Ala)-A8B) (SEQ ID NO: 17). Another example of such a suitable linker is Cys-(Gly-Gly-Gly-Gly-Ser)$_2$ (SEQ ID NO: 19).

If the mutein carries a cysteine as C-terminal residue (cf. the muteins A813-Cys71 and A8B-Cys73), the dimerization can also occur by coupling of two muteins via these C-terminal cysteine residues as described by Pellas et al., "Novel C5a receptor antagonists regulate neutrophil functions in vitro and in vivo," Journal of Immunology, Jun. 1, 1998, pp 5616-5621, vol. 160, no. 11, incorporated herein by reference. The dimerization can also be achieved by linking a nucleotide sequence encoding a mutein in an appropriate reading frame with the nucleotide sequence coding for a protein which forms a homodimer in its native fold. Subsequent expression of the nucleic acid molecule yields a fusion protein consisting of the dimerization module linked to the C5a mutant polypeptide, which then dimerizes spontaneously. Examples of such proteins which can be used as dimerization modules are alkaline phosphatase, superoxide-dismutase or glutathione-S-transferase. The use these proteins is in particular useful because the respective functional fusion protein can readily be obtained by periplasmic expression in bacterial expression systems such as E. coli. The use of dimerization modules such as alkaline phosphatase or superoxide-dismutase provides the further advantage that such a fusion protein can easily be detected using a chromogenic reaction which is catalyzed, e.g., by alkaline phosphatase. Suitable chromogenic substrates for these enzymes, such as 5-bromo-4-chloro-3-indolylphosphate for alkaline phosphatase, are well known to the person skilled in the art. Those fusion proteins are therefore suitable as diagnostic reagents.

In accordance with the disclosure of the above paragraph, the mutein of the invention is in a further embodiment linked to a protein or a peptide tag, i.e., in which a fusion protein containing the C5a mutein is also part of the invention. However, the fusion proteins of the mutein A8B with Jun/Fos alone, and, with Jun/Fos and the minor coat protein (pIII) of the filamentous M13 phage fused to the N-terminus of the mutein A8B, which are known from Heller et al, "Selection of a C5a receptor antagonist from phage libraries attenuating the inflammatory response in immune complex disease and ischemia/reperfusion injury," Journal of Immunology, Jul. 15, 1999, pp 985-994, vol. 163, no. 2, are excluded from the invention. The same applies to the mutein A8B that has a hexahistidine tag directly fused to the N-terminus, because this polypeptide is known from Hennecke, Untersuchung zur C5a-C5a Rezeptor-Interaktion unter Verwendung des Phage-Displays, PhD thesis, 1998, Medical School Hannover, Germany.

A fusion protein of the invention can comprise any suitable fusion partner, e.g., alkaline phosphatase or the green fluorescent protein (GFP) as long as the fusion partner does not interfere with the antagonistic properties of the mutein disclosed here and converts the mutein into an agonist when given to a patient, for example. A fusion partner appropriate for therapeutic purpose is a protein such as albumin which can enhance the in vivo (circulation) half-life of a mutein of the invention. The fusion partner can be fused to the N-terminus of the C5a mutein. Likewise, any peptide tag can be fused to the N-terminus of the mutein as long as its antagonistic property is maintained. Examples of suitable affinity tags are the STREP-TAG® which has specific binding affinity for streptavidin or mutants thereof as STREP-TACTIN® (see U.S. Pat. No. 5,506,121, Skerra et al., issued Apr. 9, 1996, and U.S. Pat. No. 6,022,951, Sano et al., issued Feb. 8, 2000, both incorporated by reference herein), the Flag-tag or the myc-tag, all of which can be used for purification of the mutein by affinity chromatography.

It should, however, be noted that in the event of, e.g., inventive C5a muteins conjugated or fused to a partner that confers agonistic properties, the antagonistic muteins can be readily generated/released from its (fusion) partner by treatment such as limited proteolysis or cleavage, for example enzymatic or chemical cleavage, of a (peptide) bond which links the C5a mutein to the (fusion) partner. Accordingly, it is also within the scope of the present invention, to use a fusion partner, for example, for improved purification of the mutein, for example, even if this fusion partner confers an agonistic activity as long as this activity can be eliminated before (and thus the antagonistic activity of the inventive mutein is generated) the muteins is used, for instance, in a desired therapeutic application. It is also possible to use a mutein the antagonistic activity of which is reduced by the (fusion) partner but not completely abolished. In this case, it is thus not necessary to deliberate the mutein of the invention by cleavage from its (fusion) partner. Rather, the fusion protein or the conjugate as explained in the following can be used in a desired application.

The mutein used in the present invention can also be conjugated to a protein or a different chemical (macromolecular) moiety via a suitable peptidic or non-peptidic linker that can be attached to any suitable residue within the primary sequence of the mutein. A protein can, for instance, be conjugated with the C5a mutein using solvent exposed α-amino groups of lysine residues and glutaraldehyde as linker. Another suitable coupling chemistry is amine-amine crosslinking using bis(succinimidylesters) of 5,5'-dithiobis-(2-nitrobenzoic acid) (DTNB) as described in Haugland, R. Handbook of Fluorescent Probes and Research Chemicals, 6th Ed. 1996, Molecular Probes, Eugene, Oreg., on page 96, incorporated herein by reference. Any protein can be coupled to the C5a mutein, depending on the desired application. For example, a conjugate with streptavidin, horseradish peroxidase or green fluorescent protein might be used as a diagnostic reagent or research tool for visualizing a C5a receptor on the surface or within different compartments of a cell.

In a preferred embodiment a mutein of the invention is conjugated to a moiety which enhances the in vivo half-life of the mutein. Such a conjugate is particularly useful when a present C5a receptor antagonist is used for the treatment of the organ recipient where a long term presence of the antagonist within the graft is desired. Suitable moieties are proteins such as human serum albumin. It is also possible to use a non-protein (macromolecular) moiety such as polyethylene glycol.

The C5a muteins including conjugates or fusion proteins thereof are useful in the treatment and/or prevention or prophylaxis of a variety of injurious conditions or diseases in which the complement system, and more particularly C5a and the C5a receptor, are involved. They are therapeutically very suitable when administered to any mammal such as cats, dogs, monkeys, rabbits, mice, rats and, of course, especially humans that face a high risk of C5a-mediated tissue destruction and death. In general, the conditions or diseases are usually those such as inflammatory disorders where C5a is generated proteolytically in serum or tissue.

The preservation solution also preferably includes pharmaceutically-acceptable adjunct materials, such as ethylene diaminetetraacetic acid (EDTA) in an amount from 0.5 µM to about 1.5 µM as a chelating agent (or other chelating agents known in the art may also be used). It has also been found desirable to add from 10 µM to about 100 µM of caprylic acid which helps the solution to bypass blocked fatty acid utilization and from 10 µg/L to 100 µg/L of apoferritin which serves to eliminate iron ($Fe^{++}$) which causes breakdown of the cells. Desferrioxamine may also be used to chelate the iron. Dichloroacetic acid may be employed to reduce lactate.

Suitable pharmaceutically acceptable antioxidants include, but are not limited to, allopurinol, glutathione, beta-carotene, catalase, superoxide dismutase, dimethyl thiourea (DMTU), diphenyl phenylene diamine (DPPD), mannitol or cyanidanol in an amount effective to inhibit the generation of oxygen-derived free radicals. The antioxidants are present generally in an amount from about 1 µM to 10 µM. Antibiotics may be added for transplantable organs, but are not generally added during acute studies.

The transplantation method of the present invention is to preserve and store the organ with the preservation solution and reperfuse with preservation solution prior to implantation. In a preferred method, the surgeon removes the organ and connects it to a perfusion apparatus comprising tubing and pumps. The preservation solution is then perfused through the organ while gassed with oxygen and carbon dioxide while it is awaiting implantation into a patient. A perfusion rate of from about 25 to about 150 mL/hour, preferably about 50 mL/hour, at 1° C. has been found to be effective. This organ perfusion can occur at either a constant flow or pressure. In a variation of this method, after the donor has died, but before the organs have been removed from the donor, the donor's body can be perfused with the preservation solution of the present invention in order to provide the beneficial effects of the solution to the organs at the earliest possible time. Once the organs are removed, they are then perfused with the preservation solution as described above.

The preservation solution can be used at all temperatures ranging from 0° C. to normal body temperature, 37° C. At temperatures of from about 12° C. to about 37° C. the solution is particularly effective.

The following example is provided to further illustrate the present invention and is not intended to be construed as limiting the invention in any manner.

Example

A liter of preservation solution having the following composition is prepared.

TABLE 2

| Component | Concentration |
|---|---|
| NaCl | 118 mM |
| KCl | 30 mM |
| $CaCl_2$ | 1.75 mM |
| $KH_2PO_4$ | 1.2 mM |
| $MgSO_4$ | 1.2 mM |
| $NaHCO_3$ | 25 mM |
| Glucose | 11 mM |
| Adenosine | 10 µm |
| EDTA | 1.0 mM |
| DMA | 1.0 µm |
| Heparin | 1000 units |
| Distilled, deionized water | q.s. |

To this solution is added the C5a mutein in sterile water or other sterile injectable medium to reach a final concentration in the preservation solution of from about 0.1 to about 10 µM. The C5a mutein used has the following structure:
SEQ ID NO: 16 (C5a-(1-66,Cys27Ala)-ABB-Del. 71-73).

The preservation solution defined above is perfused through a kidney or a heart, at a rate of about 50 mL per hour, after removal from the donor and prior to implantation. Similar results are obtained when the specific C5a mutein component utilized is replaced, in whole or in part, with the following:
SEQ ID NO: 9 (C5a-(1-66, Cys27Ala)-A8B);
SEQ ID NO: 10 (C5A-(1-66, Cys27Ala)-A8B-Leu 70);
SEQ ID NO: 11 (C5a-(1-66, Cys27Ala)-A8B-Cys71);
SEQ ID NO: 12 (C5a-(1-66, Cys27Ala)-A8B-Cys73);
SEQ ID NO: 13 (C5a-(1-66, Cys27Ala)-A8B-Leu70-Tyr73);
SEQ ID NO: 14 (C5a-(1-66, Cys27Ala)-A8B-Lys69-Ala70);
SEQ ID NO: 15 (C5a-(1-66, Cys27Arg)-A8B);
SEQ ID NO: 17 (C5a-(1-66, Cys-3,Gly-2,-1,Cys27Ala)-A8B); and
SEQ ID NO: 18 (C5a-(1-66, Cys27Ala)A5a).

The present invention has been described in detail and with particular reference to the preferred embodiments. Those skilled in the art will appreciate that changes can be made without departing from the spirit and scope thereof. Accordingly, the present invention is to be defined by the following claims, with equivalents of the claims to be included therein.

What is claimed is:

1. A preservation solution for storage and reperfusion of organs for implantation comprising: (a) a balanced isotonic solution comprising sodium, potassium, calcium, and magnesium ions, and glucose and sodium bicarbonate, in a physiologically acceptable amount; (b) a safe and effective amount of a C5a receptor antagonist comprising a mutein of the C5a anaphylatoxin, wherein the amino acid residue at sequence position 69 is mutated; and (c) water.

2. The preservation solution according to claim 1 which contains from about 0.1 µM to about 10 µM of the C5a mutein.

3. The preservation solution according to claim 2 wherein, in the mutein, the amino acid residue at sequence position 69 is replaced by leucine or a positively charged amino acid residue.

4. The preservation solution according to claim 2 wherein, in the mutein, the amino acid residue at sequence position 67 is mutated.

5. The preservation solution according to claim 2 wherein, in the mutein, at least one of the amino acid residues at sequence positions 70 to 74 of the natural amino sequence is mutated or at least one of the amino acid residues at said sequence positions 70 to 74 is deleted.

6. The preservation solution according to claim 3 wherein, in the mutein, the positively charged amino acid residue at sequence position 69 is Arg or Lys.

7. The preservation solution according to claim 4 wherein the mutein comprises at sequence position 67 an aromatic amino acid selected from the group consisting of Phe, Trp and Tyr.

8. The preservation solution according to claim 5 wherein the mutein comprises a hydrophobic amino acid residue at sequence position 70.

9. The preservation solution according to claim 8 wherein the mutein comprises Leu or Ala at sequence position 70.

10. The preservation solution according to claim 5 wherein the mutein comprises Ser at sequence position 70.

11. The preservation solution according to claim 2 wherein the mutein comprises a terminal sequence selected from the group consisting of SEQ ID NO: 1; SEQ ID NO: 2, SEQ ID NO: 3, SEQ ID NO: 4, SEQ ID NO: 5, SEQ ID NO: 6, SEQ ID NO: 7, and SEQ ID NO: 8.

12. The preservation solution according to claim 2 wherein the mutein further comprises Arg at sequence position 27.

13. The preservation solution according to claim 2 wherein the mutein has an amino acid sequence selected from the group consisting of SEQ ID NO: 9, SEQ ID NO: 10 SEQ ID NO: 11, SEQ ID NO: 12, SEQ ID NO: 13, SEQ ID NO: 14; SEQ ID NO: 15; SEQ ID NO: 16; SEQ ID NO: 17; SEQ ID NO: 18.

14. The preservation solution according to claim 2 wherein the mutein is fused to a protein or a peptide tag with the proviso that the fusion proteins of the mutein A8B with Jun/Fos alone or with Jun/Fos and the minor coat protein (pIII) of the filamentous M13 phage mutein A8B, wherein the Jun/Fos moiety is fused to the N-terminus of the mutein A8B, as well as the mutein A8B having a hexahistidine tag directly fused to the N-terminus are excluded.

15. The preservation solution according to claim 2 wherein the mutein is conjugated to a protein moiety via a suitable peptidic or non-peptidic linker which enhances the in vivo half-life of the mutein.

16. The preservation solution according to claim 1 wherein the solution comprises from about 10 µM to about 100 µM caprylic acid.

17. The preservation solution according to claim 1 wherein the solution comprises from about 10 µg/L to about 100 µg/L apoferritin.

18. The preservation solution according to claim 1 wherein the solution comprises desferrioxamine.

19. The preservation solution according to claim 1 wherein the solution comprises dichloroacetic acid.

* * * * *